(12) United States Patent
Bauer

(10) Patent No.: US 7,591,390 B2
(45) Date of Patent: Sep. 22, 2009

(54) STERILIZATION CONTAINER LATCH MOUNTING SYSTEM

(76) Inventor: Witold Bauer, 27715 Woodpath Tri., Westlake, OH (US) 44145

( * ) Notice: Subject to any disclaimer, the term of this patent is extended or adjusted under 35 U.S.C. 154(b) by 547 days.

(21) Appl. No.: 11/157,383

(22) Filed: Jun. 20, 2005

(65) Prior Publication Data

US 2006/0286005 A1    Dec. 21, 2006

(51) Int. Cl.
 *B65D 45/16* (2006.01)
 *B65D 25/28* (2006.01)
(52) U.S. Cl. .................... 220/324; 220/756
(58) Field of Classification Search ............ 220/752; 292/247, 246, 248, 256.5
 See application file for complete search history.

(56) References Cited

U.S. PATENT DOCUMENTS

| | | | | |
|---|---|---|---|---|
| 1,686,969 A | * | 10/1928 | Hebden ................ 220/810 |
| 2,300,509 A | * | 11/1942 | Komenak ................ 70/76 |
| 2,559,681 A | * | 7/1951 | Senseman ............. 292/250 |
| 2,713,506 A | * | 7/1955 | Wickstrom .......... 292/341.18 |
| 2,969,891 A | * | 1/1961 | Presnick ............... 220/640 |
| 3,030,137 A | * | 4/1962 | Tomkinson et al. ..... 292/113 |
| 3,043,616 A | * | 7/1962 | Magnuson ............. 292/3 |
| 3,464,579 A | * | 9/1969 | Asenbauer ............ 220/4.21 |
| 3,561,918 A | * | 2/1971 | Ray .................... 422/119 |
| 4,915,913 A | | 4/1990 | Williams et al. ........ 422/119 |
| 5,024,471 A | * | 6/1991 | Kahl et al. ............ 292/97 |
| 5,139,294 A | * | 8/1992 | Ward et al. ............ 292/246 |
| 5,193,706 A | * | 3/1993 | Hanna et al. ........... 220/324 |
| 5,370,254 A | * | 12/1994 | Hardigg et al. ......... 220/4.22 |
| 5,451,379 A | * | 9/1995 | Bowlin, Jr. ............ 422/297 |
| 5,626,373 A | * | 5/1997 | Chambers et al. ....... 292/113 |
| D429,820 S | * | 8/2000 | Meske et al. ........... D24/217 |
| 6,880,869 B2 | * | 4/2005 | Schainholz et al. ..... 292/307 A |
| D542,928 S | * | 5/2007 | Bauer ................. D24/217 |
| 2003/0010783 A1 | * | 1/2003 | Prezelin .............. 220/324 |
| 2005/0139599 A1 | * | 6/2005 | Schainholz et al. ..... 220/324 |
| 2005/0189773 A1 | * | 9/2005 | Tsai et al. ............ 292/241 |
| 2006/0162210 A1 | * | 7/2006 | Bauer ................. 40/658 |

* cited by examiner

*Primary Examiner*—Anthony D Stashick
*Assistant Examiner*—Robert J Hicks
(74) *Attorney, Agent, or Firm*—Brinks Hofer Gilson & Lione

(57) ABSTRACT

The invention described herein includes a support assembly for a dual latch mechanism on a sterilization container, wherein the support assembly has improved structural rigidity and integrity for repeated usage. The support assembly comprises a pair of spaced apart blocks welded directly onto the exterior surface of the tray component of a sterilization container; wherein each of the blocks hingedly receive a lower latch plate of the dual latch mechanism. The invention further provides a dual latch mechanism for a sterilization container comprising the improved support assembly. The invention also provides a manufacturing process for sterilization containers having a lid component and tray component and dual latch mechanism, wherein the process comprises directly spot-welding two blocks in spaced apart position onto the exterior surface of the tray component.

18 Claims, 6 Drawing Sheets

STERILIZATION CONTAINER LATCH MOUNTING SYSTEM

FIELD OF THE INVENTION

The invention relates to the field of medical devices. In particular, the invention pertains to latching mechanisms used to secure lids and trays to one another in sterilization containers.

BACKGROUND OF THE INVENTION

A number of mechanisms to securely and removably attach lids to medical sterilization containers are known. A tightly sealed container system is important to the successful operation of medical sterilization containers, which should avoid compromise and entry of environmental contaminants upon removal of the container from an autoclave, for example.

One such lid and tray attachment system is the dual latch system for sterilization containers as described in Williams et al., U.S. Pat. No. 4,915,913. The support structure described in Williams et al. is depicted in detail in FIGS. 15 and 16 of Williams et al. This latch system support structure includes an elongated rectangular portion having two outstanding or protruding end portions coupled to each respective end of the rectangular potion. Each of the protruding end portions contains a hinge opening for receiving the hinge posts of one of the latch components. The rectangular portion of this support structure is attached to the side of the container by accommodating four attachment posts which, in turn, are welded onto the side of the container.

One problem encountered with this support structure is mechanical failure. Partially as a result of the number of couplings utilized in the assembly of the support structure of the Williams latch, the support assembly is susceptible to metal fatigue and separation of the support bar from the side of the container. Consequently, the dual latch mechanism, which depends upon the secure fixation of the support structure, separates and becomes inoperative. In turn, the barrier between the interior container environment and the exterior environment can be compromised.

Furthermore, the successful and smooth operation of the dual latch system requires taught fixed relationships between the components that are to be permanently attached. Thus, even if the couplings of the support structure are loosened but not separated, the dual latch mechanism can be more difficult to operate due to the physical instability of the support assembly.

There is a need in the medical field for sterilization containers for dual latch assemblies having improved structural integrity. Furthermore, there is a need for support assemblies used in conjunction with dual latch mechanisms having more physically stable attachment to the sterilization container and having a sturdier construction.

SUMMARY OF THE INVENTION

The invention provides a support assembly for dual latch mechanisms for sterilization containers, said support assembly affording enhanced long-term structural integrity and sturdiness for repeated usage. It has been discovered that in addition to improved attachment integrity, a support assembly can be designed that utilizes significantly fewer components and materials. The invention also provides a support assembly that is directly attached or welded onto the container surface without relying on the use of intermediate coupling structures, such as studs, posts or plates, on the sterilization container exterior surface for fixation of the latch mechanism. The need for complex secondary structures between the latch mechanism and container surface to facilitate attachment is removed.

The invention is particularly useful in multi-component or complex latching mechanisms for sterilization containers wherein sturdy assembly and precise relationships between the various interacting components is directly related to its operational success. It has been further been discovered that the improved support assembly can also be easily configured to accommodate secondary structures, such as card holders and indicator arrows.

The invention provides a support assembly for the lower latch plate in a dual latch mechanism on sterilization containers having lid and tray components. The support assembly comprises a pair of spaced apart blocks, each welded directly onto the exterior surface of the tray component of the sterilization container, wherein each of the blocks hingedly receive one end of the lower latch plate.

The invention further provides dual latch mechanism for a sterilization container comprising a lid and tray component, the mechanism comprising: an upper latch subassembly associated with the lid component comprising a upper hinged latch plate hingedly connected to the exterior surface of the lid; a lower latch subassembly attached to the exterior surface of said tray component and comprising a lower hinged latch plate, the upper and lower hinged latch plates being reversibly engageable with one another to secure the lid to the tray; wherein the lower latch subassembly comprises a support assembly comprising a pair of spaced apart blocks welded directly onto the exterior surface of said tray. Each end of the lower latch plate is hingedly connected to the tray through one of the blocks.

Each of the blocks can be structured to accommodate secondary features useful in conjunction with dual latch mechanisms, such as card holders, indicators, carrying handles, and the like. Such secondary features can be accommodated by the support assembly by configuring the block accordingly.

The invention further provides a process for manufacturing a sterilization container having a lid component and tray component and dual latch mechanism, said process comprising directly spot-welding two blocks in spaced apart position onto the exterior surface of the tray component.

BRIEF DESCRIPTION OF THE DRAWINGS

The invention is further illustrated by the following figures, none of which is to be construed as necessarily limiting the invention as to the particular embodiments shown.

DETAILED DESCRIPTION OF THE INVENTION

The invention can be used with sterilization container systems containing a lid component and tray component to be securely and removable attached to one another. Dual latch mechanisms, such as that described for use with the invention, provide a means to securely and removably engage the lid with the tray. The dual latch mechanism generally comprises an upper latch plate hingedly attached to the lid, and lower latch plate hingedly attached to the tray, wherein the upper latch plate and lower latch plate are structured to reversibly engage one another to secure the lid onto the tray. The improved support assembly of the invention can be used with the lower latch subassembly to enhance the sturdiness and precision of the dual latch mechanism as a whole, thereby improving its functionality and operation.

Figure 1:
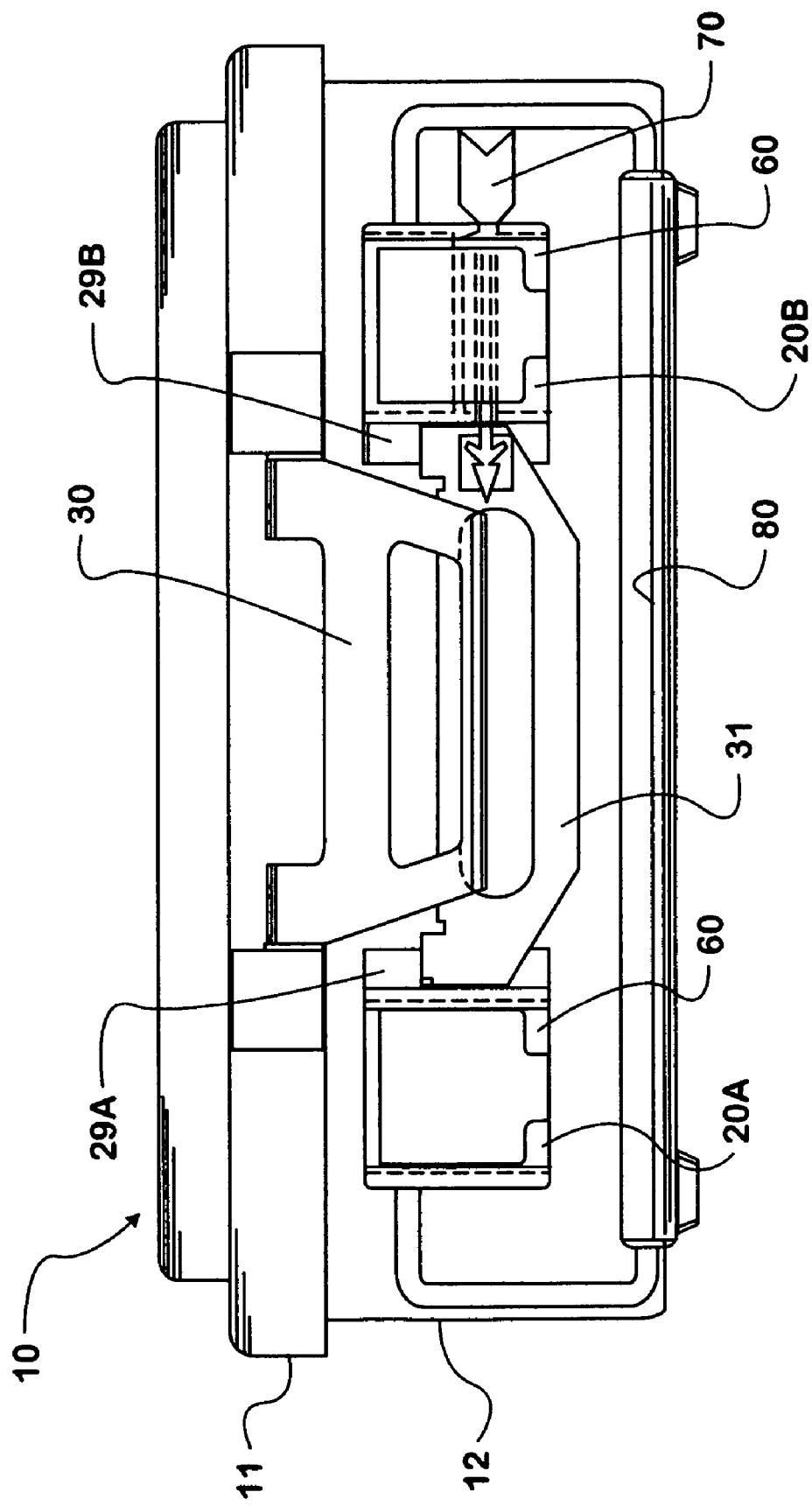
FIG. 1 is a side view of an assembled sterilization container assembly showing tray and lid components and having a dual latch system in accordance with one embodiment of the invention.

In general, one of the advantages of the invention is that the support assembly for the dual latch mechanism is attached or welded directly onto the exterior surface of the container—without requiring the use of posts, intervening plates, and the like. Referring to FIG. 1, the support assembly consists of a pair of spaced apart blocks 20A and 20B, welded directly onto the exterior surface of the tray component 12 of a sterilization container assembly 10. Each block of 20A and 20B is structured to hingedly receive the lower latch plate 31 of a dual latch mechanism. As used herein, the term "block" is used to refer to a general shape of one embodiment of the component, and variations in shape, e.g., rectangular shapes, are possible provided such shapes can share the function and advantages of the invention.

In one embodiment, the dual latch mechanism comprises an upper latch subassembly associated with the lid 11 comprising a upper latch plate 30 hingedly connected to the lid component 11, and a lower latch subassembly attached to the exterior surface of the tray component 12. The lower latch subassembly can comprise a lower hinged latch plate 31. The upper hinged latch plate 30 and the lower hinged latch plate 31 are reversibly engageable with one another as shown in FIG. 1, for example.

Figure 2:
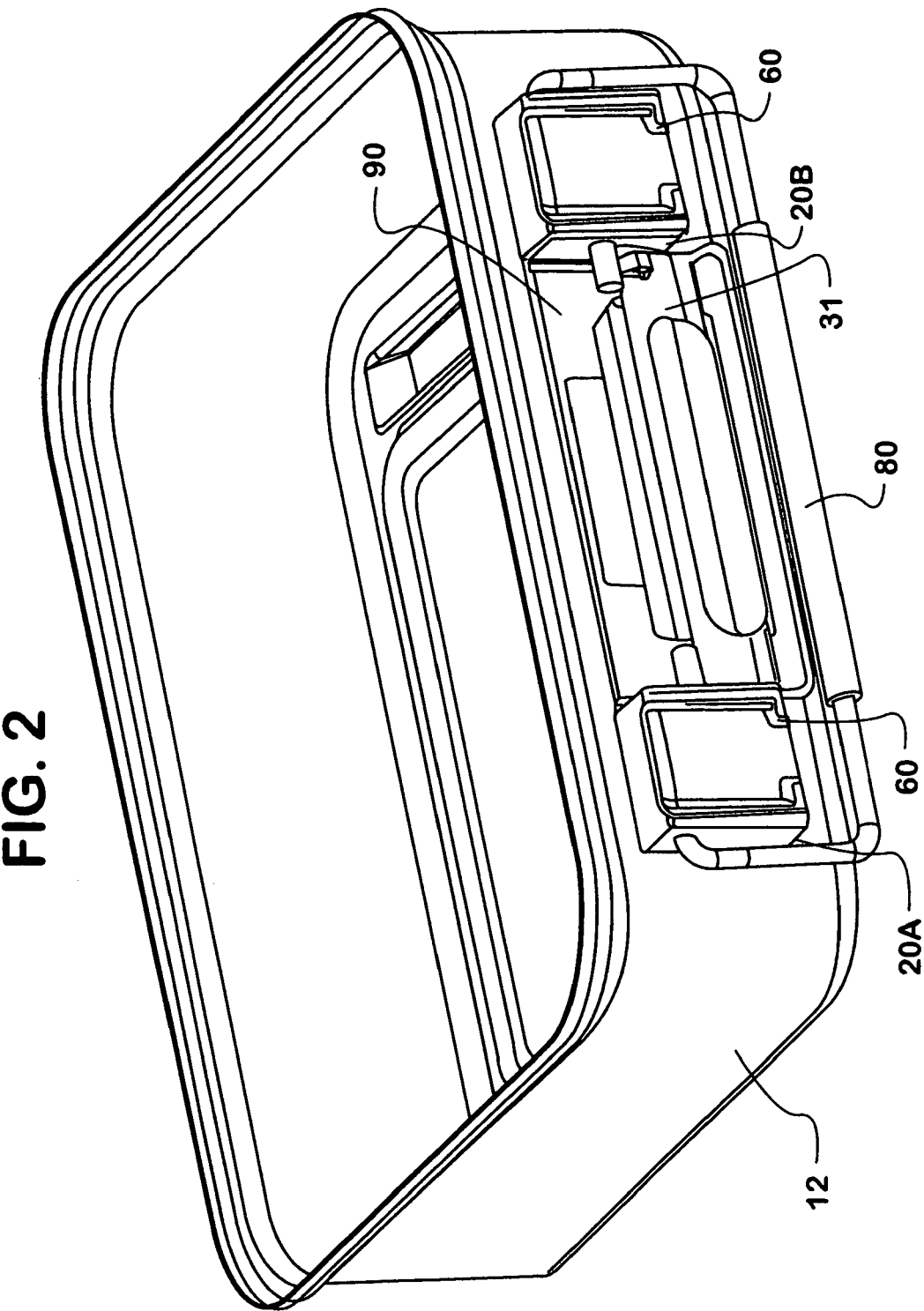
FIG. 2 is an angled side view of a tray component of a sterilization container system and showing the lower latch subassembly according to one embodiment of the invention.
Figure 3:
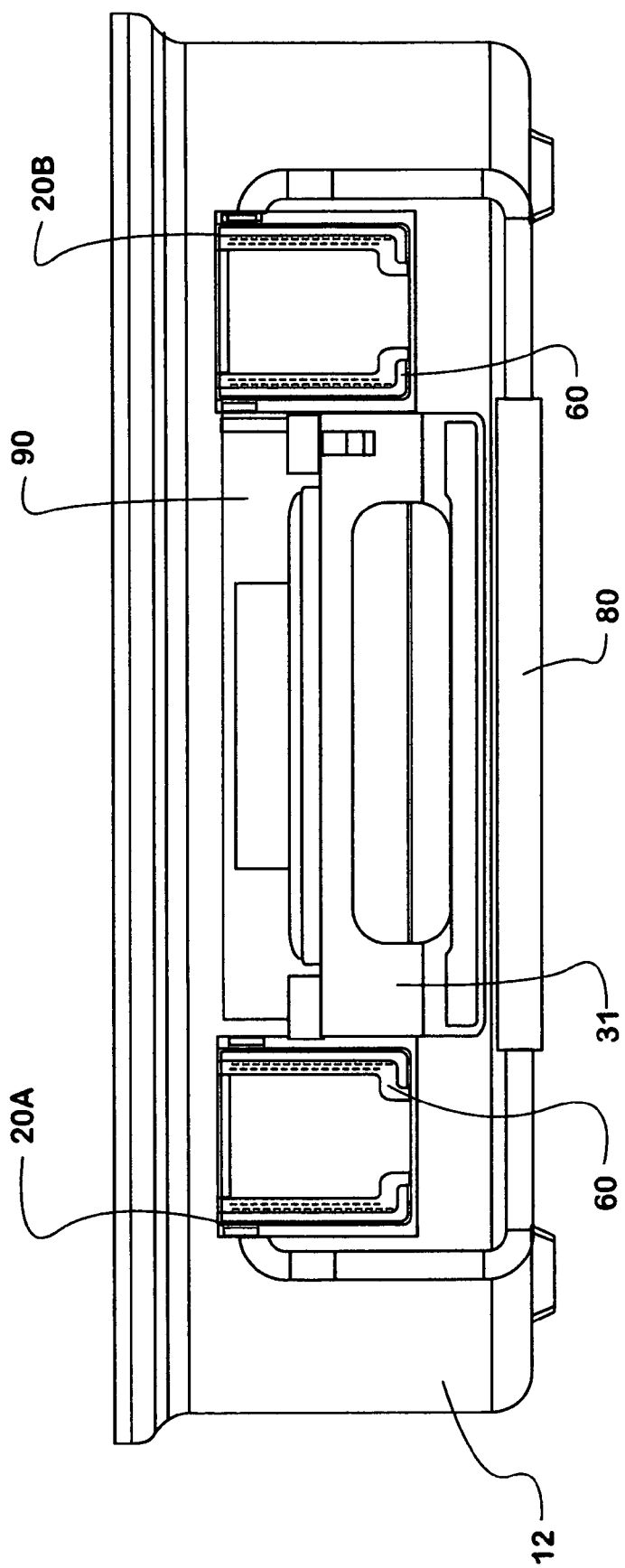
FIG. 3 is a side view of a tray component of a sterilization container system and showing the lower latch subassembly according to one embodiment of the invention.
Figure 4:
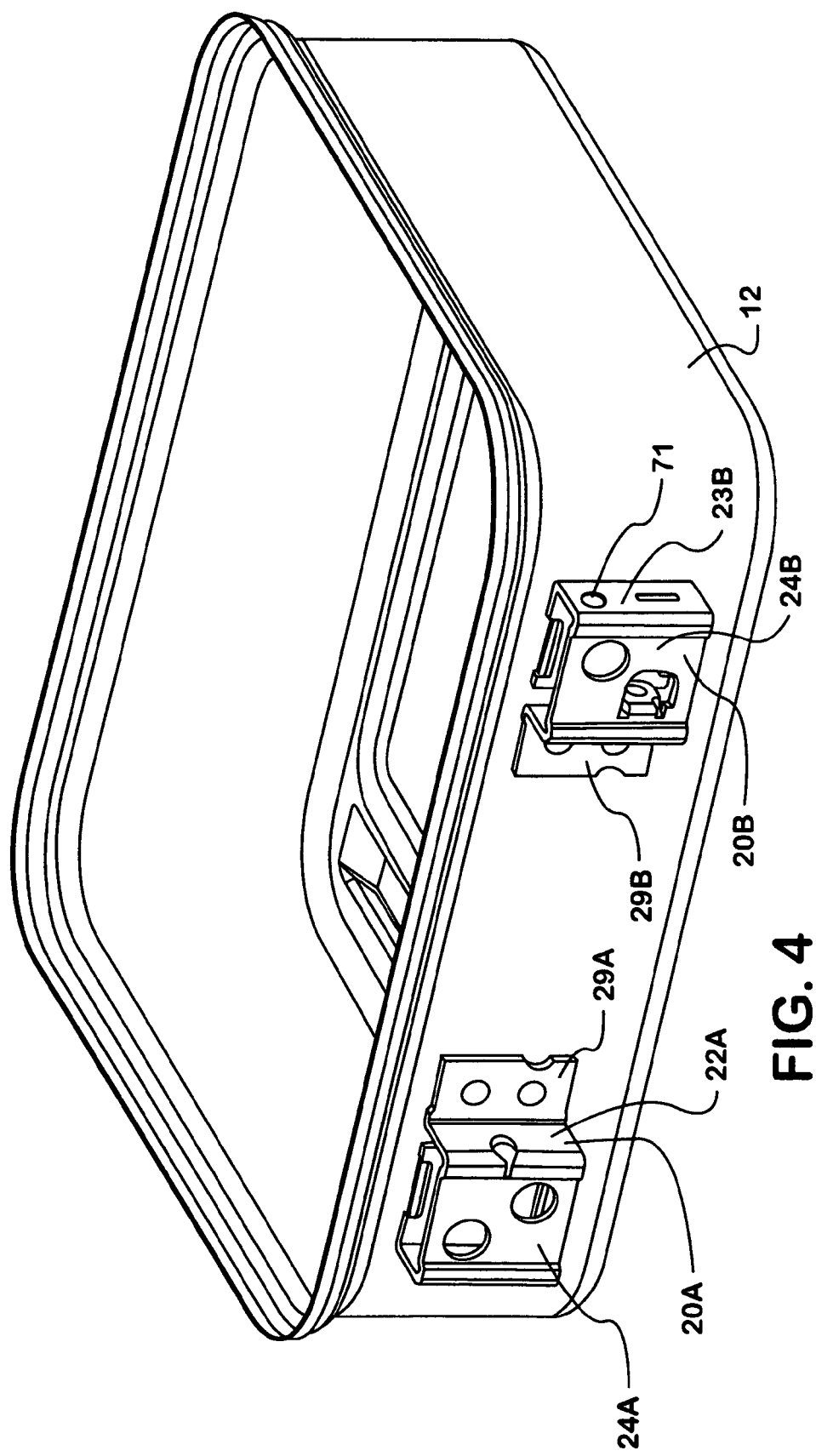
FIG. 4 is an angled side view of a tray component showing the support assembly attached to the side of the tray wall in accordance with one embodiment of the invention.

Referring now to FIGS. 2, 3 and 4, the lower latch subassembly comprises a support assembly consisting of a pair of spaced apart blocks (first block 20A and second block 20B), each of the blocks being welded directly onto the exterior surface of the tray component 12 (as shown in FIG. 4). Each end of the lower latch plate 31 is hingedly connected to each block 20A and 20B of the support assembly, such that said lower latch plate 31 is hingedly connected to the exterior surface of the tray 12 through both of said blocks.

Figure 8:
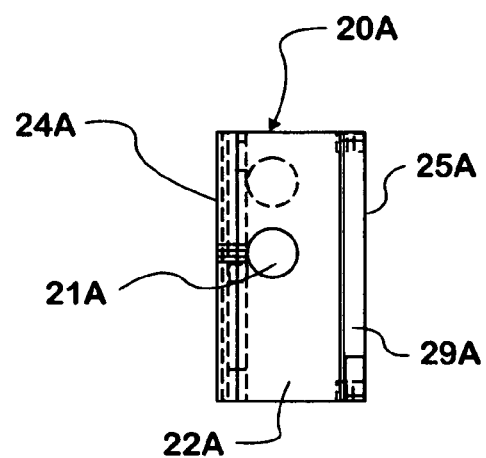
FIG. 8 is a side view of inner-facing side of one block of the pair of spaced apart blocks of the support assembly according to one embodiment of the invention.

The hinged connections of the upper latch plate 30 and the lower latch plate 31 can be accomplished through the use of various movable structures that permit the reversible engagement of the latch plates to one another. In one embodiment, the ends of the lower latch plate 31 can further comprise posts (not shown) that extend into hinge post openings 21 located on the inner-facing side 22 both of the spaced apart blocks 20A and 20B of the support assembly as shown in FIG. 8. A similar structure can be used on the lid component 11 to hingedly receive posts (not shown) extending from each end of the upper latch plate 30 (see FIG. 1).

An important aspect of the invention is that the support assembly consists of the pair of blocks, which are welded directly onto the container surface, without the use of intervening coupling structures such as posts, plates, and the like. The directness and sturdiness of the lower latch subassembly onto the container surface, which in turn mechanically interacts with the remaining components of the dual latch system, affords enhanced sturdiness and structural integrity to the whole dual latch mechanism. With the relatively reduced number of couplings to the container surface, there are consequently fewer sites for structural or mechanical failure to occur. This is important considering that sterilization containers are intended for repeated usage.

Figure 5:
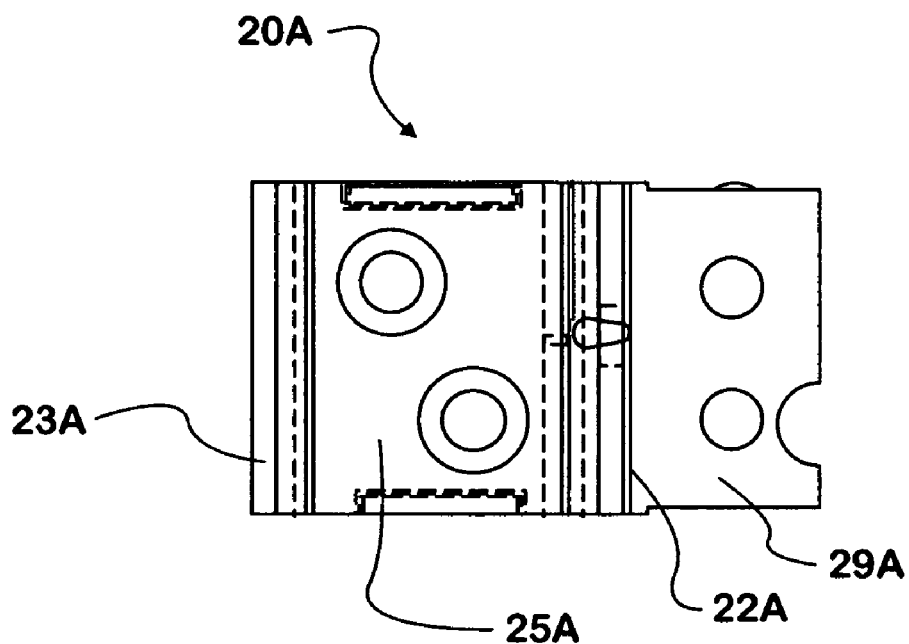
FIG. 5 is a view of the rear surface of one block of the pair of spaced apart blocks of the support assembly the according to one embodiment of the invention.

Turning now to FIGS. 4, 5, 6, 7 and 8, each of the blocks 20A and 20B can have a front surface 24 (A and B) as shown in FIG. 4 for example, rear surface 25 (A and B) as shown in FIG. 5 that attaches directly onto the exterior surface of the tray 12, an inner-facing side 22 (A and B) and an outer-facing side 23 (A and B).

Figure 6:
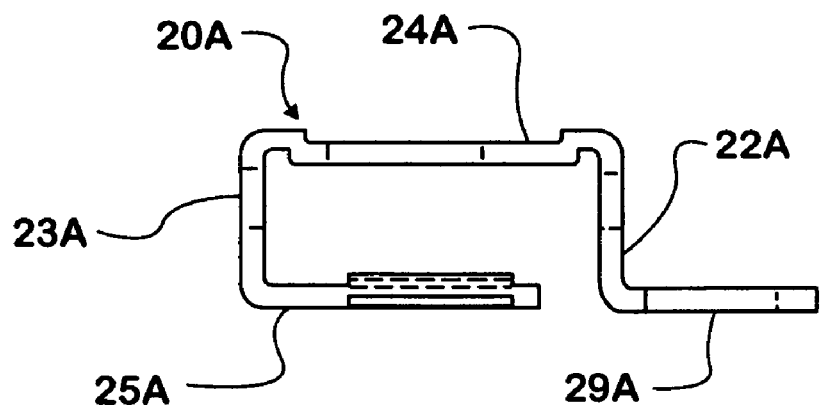
FIG. 6 is a side view of one block of the pair of spaced apart blocks of the support assembly according to one embodiment of the invention.
Figure 7:
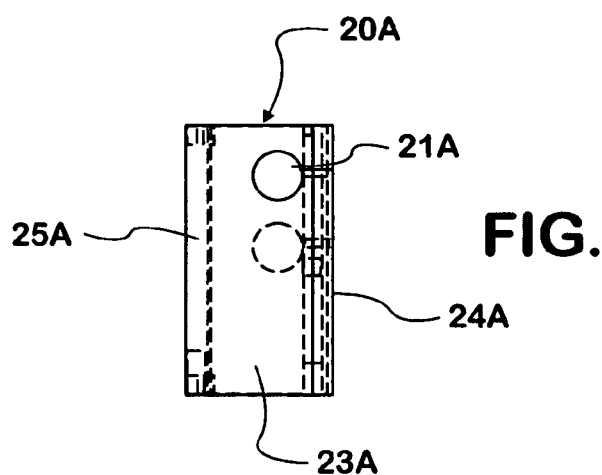
FIG. 7 is a side view of outer-facing side of one block of the pair of spaced apart blocks of the support assembly according to one embodiment of the invention.

In a preferred embodiment and as shown in FIG. 6, each of the blocks 20 is formed from an elongated planar rectangle-shaped sheet of metal. The metal sheet comprises four transverse bends so as to form an overall cuboid block as seen in FIG. 5, for example. Referring again to FIG. 6, the block further comprises a second rear surface plate 29A and 29B formed from a planar extension from one side of the block. Thus, from the side view, each block 20 (A and B) has an overall "P" shape, and each block 20 has two planar surfaces—rear surface 25 (A and B) and second rear surface plate 29 (A and B)—contacting the exterior surface of the tray component. For labeling or cosmetic reasons, second rear surface plates 29 are optionally covered or concealed by a superimposed cover plate 90 as shown in FIGS. 2 and 3.

Each of blocks 20A and 20B are directly attached to the exterior surface of the tray component. The rear surface of the block is spot-welded to the surface of the tray component using a spot-welding press. The electrodes of the spot-welding press are positioned so as to spot-weld and fuse the interfacing metal of the block surface and tray surface together. An important aspect of this process is that the metal or metallic alloy of the block component and the tray surface be the same. Examples of metal that can be used in the invention include, but are not limited to, aluminum and stainless steel. Thus, the surface of the block and tray fuse to form a contiguous, uniform metallic bond that securely and rigidly fastens the block onto the tray surface to form the support assembly.

The blocks 20 can be structured to accommodate secondary features useful in conjunction with dual latch mechanisms. Such secondary features can be accommodated by the support assembly by configuring the block accordingly, or otherwise designing the secondary feature so as not to operatively interfere with the dual latching mechanism.

In one embodiment, one or more of the blocks 20 of the support assembly can be structured to accommodate a card holder 60. Card holders used with sterilization containers can receive plates or sheets containing various kinds of information such as a description of its contents or instructions, for example. Suitable card holders can be used in conjunction with the block(s) can be those similar to that which is described in U.S. patent application Ser. No. 11/010,255 filed Dec. 13, 2004, now pending, the entire text of which is incorporated herein by reference—and as shown in FIGS. 1, 2 and 3. Card holders 60 can be composed of either plastic or metal, and can be dimensioned and structured to be superimposed over one of more of the blocks 20A and 20B of the support assembly by slide-fitting or snap-fitting, for example.

In another embodiment, one or more blocks of the support assembly can accommodate indicators. Indicators can include those having a stem-like or arrow configuration and structured to be inserted through openings in the block with one end protruding from the block and in front of the lower latch plate. Indicators of this type reveal whether the lower latch plate has been disturbed or whether the container has been opened. Suitable arrow indicators that can be used in conjunction with the invention include those described in U.S. Des. Pat. No. 429,820 and U.S. design patent application Ser. No. 29/217,385 filed Nov. 16, 2004, now pending, the entire texts of which are incorporated herein by reference—and as illustrated in FIG. 1. An arrow indicator 70 can be composed of plastic and be structured for cooperative insertion as shown in FIG. 1 through a corresponding aligned openings 71 (see FIG. 4, for example) located on both the inner-facing side 22 and outer-facing side 23 of a block 20.

In a further embodiment, the blocks of the support assembly can be structured to accommodate one or more carrying handles. One example of a suitable carrying handle that can be employed is that described in U.S. Pat. No. 4,915,913, the entire text of which is incorporated herein by reference—and as shown in FIGS. 1 2 and 3 as carrying handle 80.

INDUSTRIAL APPLICABILITY

The invention is useful in conjunction with latch mechanisms, particularly dual latch mechanisms, on sterilization containers. The support assembly imparts improved structural rigidity and sturdiness to the latch mechanism fixed to it, thereby enhancing the long-term structural integrity of the latch for repeated usage. As a result of the invention, the post-sterilization interior environment of the sterilization container is less likely to be compromised as a result of loosened fit between the lid and tray of the container which can occur over time through repeated usage.

The invention has been described herein above with reference to various and specific embodiments and techniques. It will be understood by those of ordinary skill in the art that reasonable modifications and variations of such embodiments and techniques can be made without significantly departing from either the spirit or scope of the invention defined by the claims below.

What is claimed is:

1. A support assembly for a lower latch plate in a dual latch mechanism system for a sterilization container having a lid component and tray component, said support assembly comprising:
    a pair of spaced apart blocks, each block welded directly onto an exterior surface of the tray component;
    wherein at least one of the blocks is configured in an overall "p shape," with a generally cuboid body including three inner transverse bends and one outer transverse bend forming two planar faces,
        at least one of the two planar faces comprising one of the welds directly onto the exterior surface of the tray component,
        at least one of the two planar faces forming a planar extension from a side of the generally cuboid body, said planar extension being generally co-planar with the other of the two planar faces; and
    wherein each of said blocks hingedly receives one end of said lower latch plate such that the lower latch plate is connected to the exterior surface of the tray component through both of the blocks.

2. The support assembly according to claim 1, wherein each block is spot-welded directly onto the exterior surface of the tray component.

3. The support assembly according to claim 1, wherein each of the two planar surfaces is spot-welded directly to the exterior surface of the tray component.

4. The support assembly according to claim 3, wherein said two planar surfaces and the exterior surface of the tray component each comprises a selected one of a metal or a metallic alloy that is the same in the planar surface and the exterior surface of the tray component, and the spot-weld fuses the selected one of the metal or the metallic alloy of the planar surfaces to the metal of the exterior surface of the tray component.

5. The support assembly according to claim 1, wherein both of said blocks are composed of the same metal or metallic alloy as the sterilization container surface to which they are attached.

6. A dual latch mechanism for a sterilization container comprising: a lid component and tray component hingedly attached together along one side, and a dual latch mechanism disposed opposite the one side, said dual latch mechanism comprising:
    an upper latch subassembly associated with the lid component comprising a upper hinged latch plate hingedly connected to the exterior surface of said lid component;
    a lower latch subassembly attached to the exterior surface of said tray component, said lower latch subassembly comprising a lower hinged latch plate, said upper hinged latch plate and said lower hinged latch plate being reversibly engageable with one another;
    wherein said lower latch subassembly comprises a support assembly consisting of a pair of spaced apart blocks, each of said blocks including a planar face comprising a selected one of a metal or a metallic alloy that is the same as a selected one of a metal or a metallic alloy of the exterior surface of the tray component portion, said planar face being welded directly onto the exterior surface of said tray in a manner fusing the selected one of a metal or a metallic alloy to form a contiguous metallic bond that securely fastens the block onto the tray component.

7. The dual latch mechanism according to claim 6, wherein each end of said upper latch plate is hingedly connected to said exterior surface of said lid component, and each end of said lower latch plate is hingedly connected to each of said pair of spaced apart blocks of said support assembly such that said lower latch plate is hingedly connected to the exterior surface of said tray through both of said blocks.

8. The dual latch mechanism according to claim 6, wherein at least one of said blocks is structured to accommodate a card holder.

9. The dual latch mechanism according to claim 6, wherein at least one of said blocks is structured to accommodate an indicator element inserted therethrough.

10. The dual latch mechanism according to claim 9, wherein said indicator element is an indicator arrow and is structured to interact with said lower latch plate.

11. The dual latch mechanism according to claim 6, wherein said blocks are structured to accommodate a carrying handle attached thereto.

12. The dual latch mechanism according to claim 11, wherein said carrying handle is hingedly attached to each of said blocks.

13. A sterilization container comprising:
    a lid component hingedly attached to a tray component along a first side of each, and a dual latch mechanism disposed on a second side opposite the first side, said dual latch mechanism comprising:

an upper latch subassembly associated with the lid component comprising a upper hinged latch plate hingedly connected to an exterior surface of the second side of the lid component; and a lower latch subassembly attached to an exterior surface of the second side of the tray component, where the lower latch subassembly includes a lower hinged latch plate, and the upper hinged latch plate and lower hinged latch plate are reversibly engageable with one another;

wherein the exterior surface of the second side of the tray component comprises a first material selected from a group consisting of a metal and a metallic alloy; and wherein the lower latch subassembly includes a support assembly consisting of a pair of spaced apart blocks, where each of the blocks is configured in an overall "p shape," with a generally cuboid body including three inner transverse bends and one outer transverse bend forming two planar faces, at least one of the two planar faces forming a planar extension from a side of the generally cuboid body, said planar extension being generally co-planar with the other of the two planar faces where each of the planar faces includes the same first material as the exterior surface of the tray component portion, where each planar face is welded directly onto the exterior surface of the tray in a manner fusing the first material of each to form a contiguous bond that securely fastens the block onto the tray component; and where each end of the lower hinged latch plate is hingedly attached to one of the pair of blocks such that the lower hinged latch plate is hingedly disposed between the pair of blocks.

14. The sterilization container of claim 13, further comprising a carrying handle attached to the blocks.

15. The sterilization container of claim 13, further comprising an indicator element disposed through an opening in at least one of the blocks, where the indicator is configured to indicate whether the lower latch plate has been opened.

16. The sterilization container of claim 13, wherein at least one of the blocks is structured to accommodate a card holder.

17. The sterilization container of claim 13, wherein the hinged attachment of the lower latch plate to each block comprises a pin on the latch plate engaging an opening on the block.

18. The sterilization container of claim 13, further comprising a cover plate disposed to cover the planar extensions of the blocks.

* * * * *

UNITED STATES PATENT AND TRADEMARK OFFICE
CERTIFICATE OF CORRECTION

PATENT NO. : 7,591,390 B2  Page 1 of 1
APPLICATION NO. : 11/157383
DATED : September 22, 2009
INVENTOR(S) : Witold Bauer It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1006 days.

Signed and Sealed this

Twenty-first Day of September, 2010

David J. Kappos
*Director of the United States Patent and Trademark Office*